(12) United States Patent
Nishihara (10) Patent No.: US 6,219,403 B1
(45) Date of Patent: Apr. 17, 2001

(54) RADIATION THERAPY METHOD AND SYSTEM

(75) Inventor: Susumu Nishihara, Tokyo (JP)

(73) Assignee: Mitsubishi Denki Kabushiki Kaisha (JP)

(*) Notice: Subject to any disclaimer, the term of this patent is extended or adjusted under 35 U.S.C. 154(b) by 0 days.

(21) Appl. No.: 09/369,316

(22) Filed: Aug. 6, 1999

(30) Foreign Application Priority Data

Feb. 17, 1999 (JP) ................................................. 11-038323

(51) Int. Cl.[7] ........................................................ A61N 5/10

(52) U.S. Cl. ............................................ 378/65; 378/205

(58) Field of Search ................................ 378/64, 205, 65, 378/69, 208; 250/492.3, 491.1

(56) References Cited

U.S. PATENT DOCUMENTS

| 5,039,867 | | 8/1991 | Nishihara et al. . | |
|---|---|---|---|---|
| 5,622,187 | * | 4/1997 | Carol | 378/65 |
| 5,727,042 | * | 3/1998 | Brenneisen | 378/65 |
| 5,740,225 | * | 4/1998 | Nabatame | 378/65 |

FOREIGN PATENT DOCUMENTS 553-766  *  10/1977  (SU) ........................................ 378/65

* cited by examiner

Primary Examiner—Robert H. Kim
Assistant Examiner—Irakli Kiknadze
(74) Attorney, Agent, or Firm—Rothwell, Figg, Ernst & Manbeck

(57) ABSTRACT

A radiation therapy system has a radiation therapy planning CT system and a radiation therapy apparatus. The CT system includes a system control unit, a CT scanner unit, and a therapy planning portion. The collected data obtained by the CT scanner unit is output to the therapy planning unit. The therapy planning portion creates therapy planning data such as center projection images for when performing therapy and center projection images for when performing X-ray photography. On the other hand, the radiation therapy planning apparatus includes a central control unit, an apparatus proper, and a driving control unit. The driving control unit controls in real-time the period of irradiation of radiation based on the therapy planning data from the CT scanner unit 34 and the opening/closing of the collimator 97, according to the position of the marker 9 on the fluoroscopy image photographed by the X-ray TV. Such an arrangement provides a radiation treatment method and system which does away with deterioration in precision owing to bodily movement during irradiation.

6 Claims, 9 Drawing Sheets

(IRRADIATION PLAN ACCORDING TO TIME t1)

FIG. 9B

(ACTUAL IRRADIATION ACCORDING TO TIME t2)

FIG. 10A (EXHALING)

FIG. 10B (INHALING)

RADIATION THERAPY METHOD AND SYSTEM

BACKGROUND OF THE INVENTION

1. Field of the Invention

The present invention relates to a radiation therapy method, and a radiation therapy system including a radiation therapy planning apparatus and radiation therapy apparatus, for determining the irradiation range of radiation to be aimed at a certain portion within the body of a subject such as a tumor, and controlling the actual irradiation of radiation based on a therapy plan that takes into consideration bodily movement of the patient during the irradiation period.

2. Description of the Related Art

In an arrangement wherein radiation is to be aimed at a certain portion in the body of a subject such as a tumor, determining the range of irradiation and matching the range of irradiation with the affected part by displaying the determined range of irradiation on the surface of the subject are extremely important tasks.

Known radiation therapy apparatus arrangements involve watching a tomography image from a CT apparatus or the like and a fluoroscopy image from an x-ray simulator or the like to determine the irradiation range.

That is, the tomography image from the CT apparatus con display the interior of the body of the subject with high contrast resolution, and the area to which radiation should be irradiated (i.e., the area of interest) can be relatively easily determined on the tomography image. The portion corresponding with the area of interest on the tomography image is obtained on the fluoroscopy image. With the fluoroscopy image from the X-ray simulator, the perspective of the fluoroscopy image matches the center of the irradiation of radiation, so the area of interest on the fluoroscopy image can be correlated with a corresponding portion on the surface of the subject. The range of irradiation has thus been determined qualitatively, which has been marked on the uneven surface of the subject using a marker or the like.

Figure 9A:
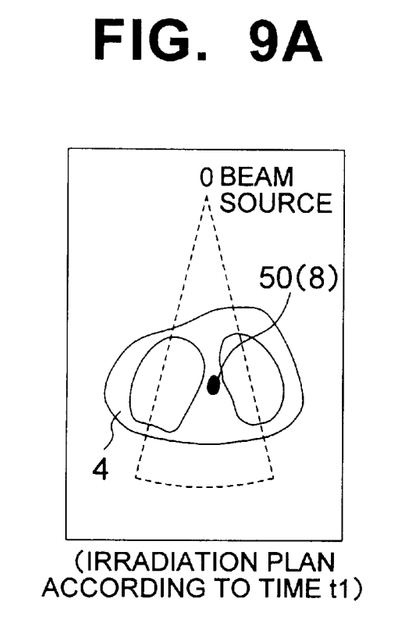
FIG. 9A is a diagram for describing known radiation therapy techniques and the problems thereof, regarding irradiation planning.

Also, the radiation therapy plan generally includes, as shown in FIG. 9A, determining a part 50 on a slice image reflecting the physical status of a subject 4 at a certain time t1, to the determining of an optimal irradiation method with the part 50 as a target 8, and the simulation thereof (In the Figure, "O" denotes a hypothetical radiation source, and the dotted arrows imply the radiation cone).

Figure 10A:
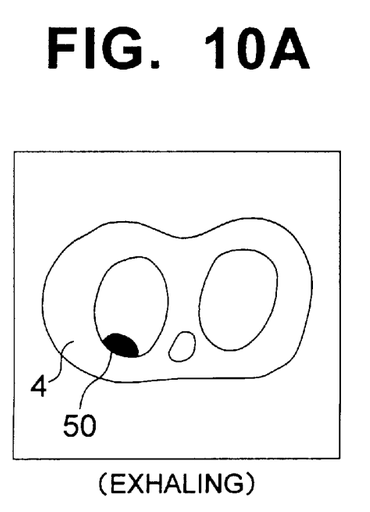
FIG. 10A is a diagram describing the exhaling period in known radiation therapy.
Figure 10B:
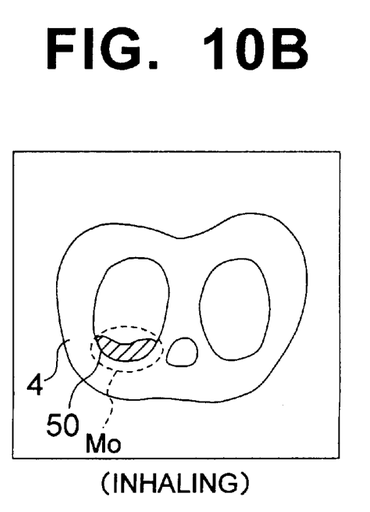
FIG. 10B is a diagram describing the inhaling period in known radiation therapy.

However, in the case of creating a therapy plan for a part which is easily affected by bodily moving caused by breathing, variations are taken into consideration for the exhaling period (shrunk) and inhaling period (stretched) of the part 50 displayed on-the slice image of the subject 4, as shown in FIGS. 10A and 10B. That is, a irradiation part including a so-called safety margin Ma is set, so as to be somewhat larger that the part 50.

Accordingly, the range of the therapy plan is set larger than the form of the part 50 which is a tumor or the like, due to bodily moving caused by breathing.

However, it is difficult to distinguish fine differences in contrast with fluoroscopy using X-ray simulators, and particularly in the event that the contrast between the area of interest and other areas is small, the area of interest determined in the tomography image has not been able to be identified in the fluoroscopy image. Thus, judging at which position in the fluoroscopy image the area of interest identified in the tomography image exists has been a troublesome task which requires much experience. Also, owing to such, it has been difficult to precisely determine the range for irradiation of radiation beams.

Also, the slice images which have been used for the therapy plan are images taken of the physical state of the patient at the time of examination, and this is also problematic in that these images do not reflect the constantly-changing bodily movements.

Figure 9B:
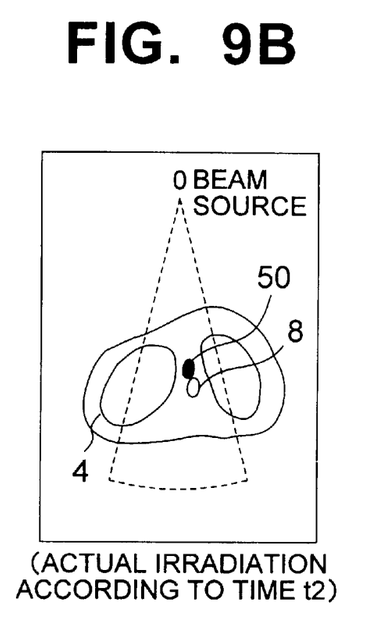
FIG. 9B is another diagram for describing known radiation therapy techniques and the problems thereof, regarding actual irradiation.

For example, with actual irradiation of radiation beams, the position of the part 50 serving as the target 8 is constantly moving from the position of the target 8 in the plan, due to bodily movement of the subject 4 such as breathing, but actual irradiation is performed according to the therapy plan with the target 8 fixed, so there has been a problem in that the target 8 of the irradiation shifts away from the actual part 50 at a time t2 during the irradiation period, as shown in FIG. 9B. This shifting of the irradiation target owing to bodily movement increases in magnitude in the case that the patient has to be subjected to the therapy for prolonged sessions.

On the other hand, setting of the irradiation portion including the safety margin Ma (See FIG. 10) depended greatly on the experience and instincts of the operator (physician), so however carefully the safety margin may be set, there has been no guarantee that the margin is sufficiently large.

Accordingly, in the event that the irradiation portion including the safety margin Ma is set to a size greater than necessary, there has been the possibility that non-tumor parts outside of the tumor portion may be subjected to excessive irradiation of radiation. Conversely, in the event that the set size is smaller than necessary, there have been problems that the amount of radiation is less than the planned standard, resulting in repeating the radiation treatment.

SUMMARY OF THE INVENTION

The present invention has been made in light of the above-described problems, and accordingly, it is an object of the present invention to provide a radiation therapy method and a radiation therapy system wherein an image suitable for determining the range for irradiation of radiation can be synthesized, and a fluoroscopy image of the subject can be synthesized on an X-ray TV simultaneously with the irradiation, thereby solving the problem of deterioration in precision of the therapy plan due to bodily movement during the irradiation period.

In order to realize the above object, according to the present invention, a radiation therapy method includes a center projection image synthesizing method for creating an image for determining the range of irradiation of radiation beams, in an arrangement wherein irradiation of radiation beams is aimed at a specific portion such as a tumor within the body of a subject, the projection image synthesizing method comprising: a step for establishing a marker at the specific portion such as tumor, or nearby (including the surface of the subject); a step for obtaining 3-D data regarding inside of the body of the subject with a CT apparatus or the like; and a step for obtaining from the 3-D data a center projection image for 3-D data according to a center-of-projection point determined beforehand and the marker, and/or an area of interest within the 3-D data; wherein the relative positions of the established marker and the specific portion are clarified, and irradiation of radiation beams is terminated in the event that the relative positions shift.

The center projection image may be an image of the subject which changes over time, and the obtained projection image data may be output to a recording medium.

According to another aspect of the present invention, the projection image synthesizing method comprises: a step for specifying as an area of interest an area corresponding with the specific portion in the 3-D data regarding inside of the body of the subject which has been obtained with a CT apparatus or the like; and a step for calculating a center projection image for the area of interest according to a center-of-projection point at geometric conditions set for the area of interest and the established marker, and/or the 3-D data; wherein the geometric conditions are the same as the geometric conditions for the point of origin for irradiation of radiation beams to the portion corresponding with the area of interest in the body of the subject.

According to another aspect of the present invention, the geometric conditions are the same as the geometric conditions for the focal point of an X-ray tube in an X-ray TV apparatus on the portion corresponding with the area of interest in the body of the subject.

The projection image obtained by the center projection image synthesizing method may be output to a recording medium.

According to another aspect of the present invention, the radiation therapy method comprises: a step for specifying as an area of interest a desired area in the 3-D data regarding inside of the body of the subject which has been obtained with a CT apparatus or the like; a step for calculating a projection image for the area of interest according to a center-of-projection point at geometric conditions set for the area of interest, and/or 3-D data; and a step for projecting the projection image on the surface of the subject by means of an optical system which has conditions that are the same as the geometric conditions for the specific portion corresponding with the area of interest in the body of the subject, wherein the center-of-projection point thereof matches the point of origin for generating radiation beams.

According to another aspect of the present invention, a radiation therapy method includes a center projection image synthesizing method for establishing a marker at a specific portion such as a tumor within the body of a subject, or nearby (including the surface of the subject), and creating an image for determining the range of irradiation of radiation beams, in an arrangement wherein irradiation of radiation beams is aimed at the specific portion such as tumor within the body of a subject that has been obtained with a CT apparatus or the like; wherein a projection image is obtained from 3-D data according to a center-of-projection point determined by 3-D data relating to the inside of the body of the subject, and/or an area of interest within the 3-D data.

According to another aspect of the present invention, a radiation therapy system uses a center projection image synthesizing method for creating an image for determining the range of irradiation of radiation beams, in an arrangement wherein irradiation of radiation beams is aimed at a specific portion such as a tumor within the body of a subject, the system comprising: a means for establishing a marker at the specific portion such as tumor, or nearby (including the surface of the subject), and for specifying as an area of interest an area corresponding with the specific portion in the 3-D data regarding inside of the body of the subject which has been obtained with a CT apparatus or the like; and a means for calculating a projection image for the area of interest according to a center-of-projection point at geometric conditions set for the area of interest and the marker, and/or the 3-D data; wherein the geometric conditions are the same as the geometric conditions for the point of origin for irradiation of radiation beams to the portion corresponding with the area of interest in the body of the subject.

According to another aspect of the present invention, the geometric conditions are the same as the geometric conditions for the focal point of an X-ray tube in an X-ray TV apparatus on the portion corresponding with the area of interest in the body of the subject.

According to another aspect of the present invention, a radiation therapy system comprises: a means for specifying as an area of interest a desired area in the 3-D data regarding inside of the body of the subject which has been obtained with a CT apparatus or the like; and a means for projecting a projection image on the surface of the subject by means of an optical system which has conditions that are the same as the geometric conditions for the specific portion corresponding with the area of interest in the body of subject according to the center-of-projection point of the geometric conditions set for the area of interest, wherein the center-of-projection point thereof matches the point of origin for generating radiation beams.

The radiation therapy system may further comprise means for enlarging or reducing the size of the projection image by a desired ratio and outputting to a recording medium.

According to another aspect of the present invention, a radiation therapy system comprises: time determining means for obtaining CT images from a subject for which a marker has been established, and at the same time detecting marker position information from the CT images according to changes in body movement of the subject from the X-ray TV performing fluoroscopy on the subject, and for correlating the detecting position information and the time of the CT images; therapy planning data creating means for creating therapy planning data including collimator open/close data, based on the marker position information by the time determining means; and control means for real-time controlling of the irradiation state of radiation during the irradiation period according to the therapy planning data created by the therapy planning data creating means and position information of the marker established on the subject.

The control means may further comprises: judging means for judging the positional relation between the position information of the marker obtained by the CT images which serve as the base for the therapy planning data, and the position information of the marker during the irradiation period; and irradiation control means for, in the event that the judging means judges that positional correlation exists, instructing irradiation of radiation, and instructing opening/closing of the collimator based on the open/close data.

According to another aspect of the present invention, a method for terminating irradiation of radiation in the event that an area of interest such as a tumor shifts from the target due to bodily movement or the like, and resuming the irradiation when the affected part returns to the position from which it shifted, is performed by grid control of a triode electron gun.

DESCRIPTION OF THE PREFERRED EMBODIMENTS

First Embodiment

The following is a detailed description of a first embodiment of the radiation therapy planning apparatus according to the present invention.

Figure 1:
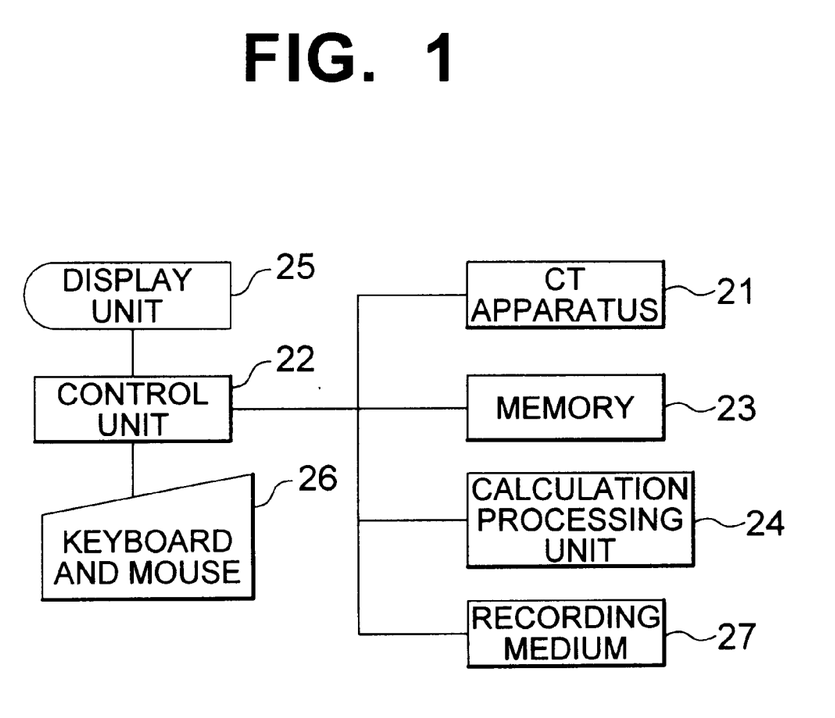
FIG. 1 is a block diagram illustrating the configuration of a radiation therapy planning apparatus according to the present invention.
Figure 2:
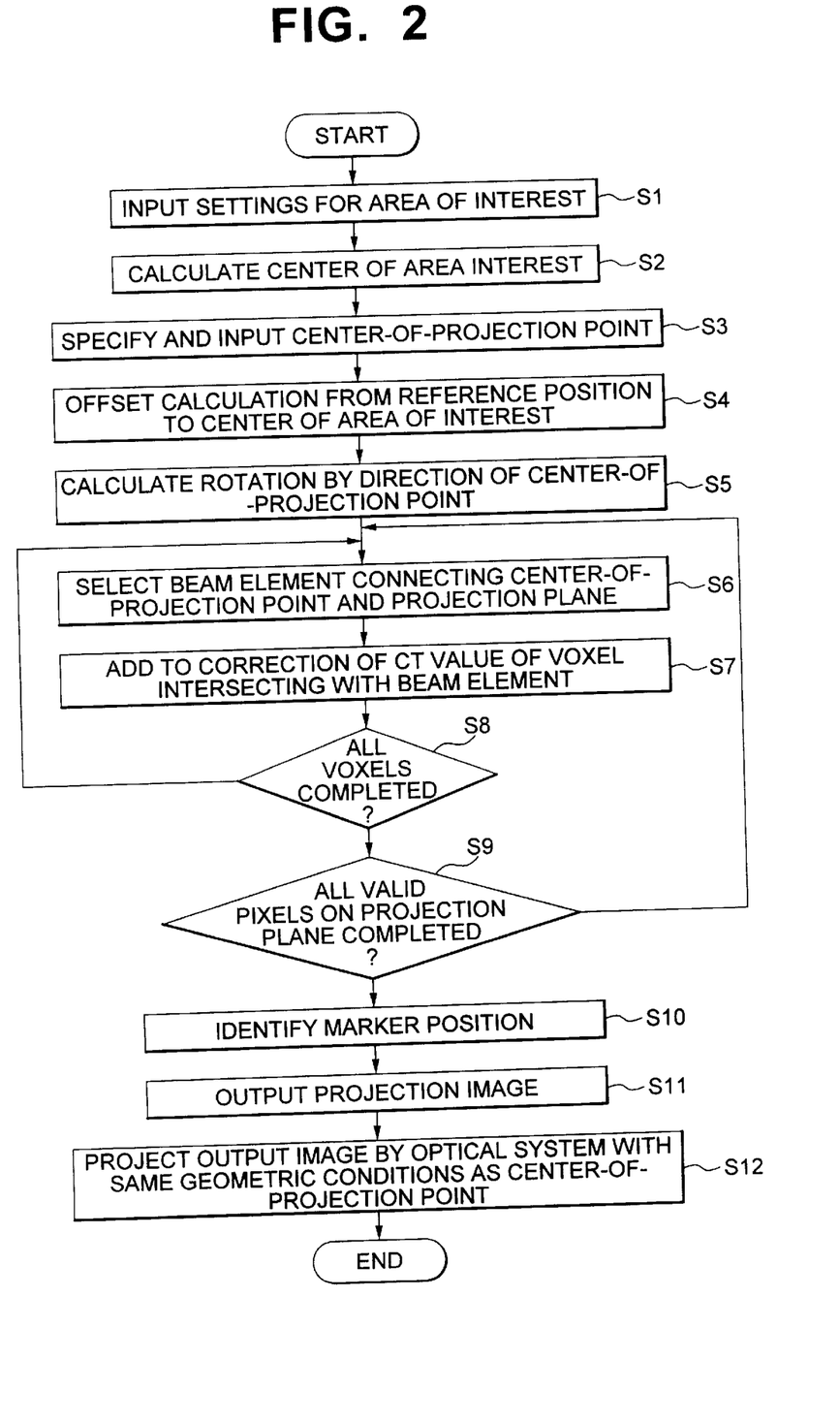
FIG. 2 is a flowchart describing the operation of the radiation therapy planning apparatus according to the present invention.
Figure 3A:
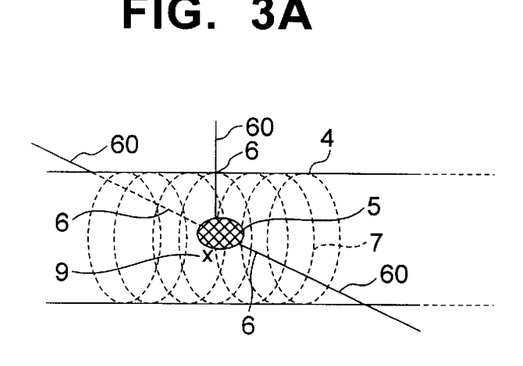
FIGS. 3A through 3C are diagrams illustrating the projection image synthesizing method according to the present invention.
Figure 3B:
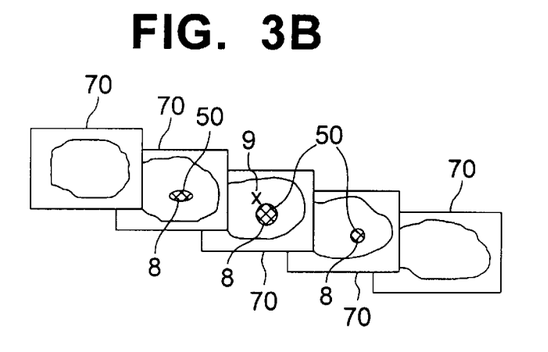
Figure 3C:
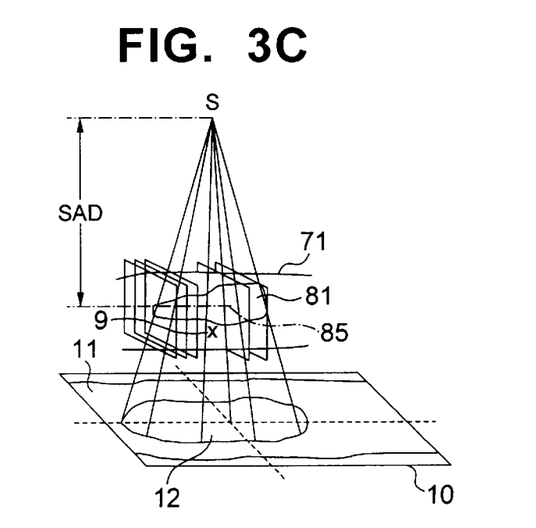

FIG. 1 is a block diagram of the radiation therapy planning apparatus according to the present invention, FIG. 2 is a flowchart describing the operation of the radiation therapy planning apparatus according to the present invention, and FIG. 3 is a diagram illustrating an embodiment of the center projection image synthesizing method according to the present invention, and a portion of an embodiment of the projection image displaying method.

In the Figures, reference numeral 21 denotes a CT apparatus which creates 3-D data based on multiple tomography images within the body of the subject, 22 denotes a control unit of a radiation therapy planning apparatus, 23 denotes memory for storing the 3-D data, 24 denotes a calculation processing unit for calculating projection images from the 3-D data, 25 denotes a display unit for displaying various images, 26 denotes a keyboard and mouse for inputting the geometric conditions for the area of interest and the center-of-projection point, and 27 denotes a recording medium to which the projected image is output.

Further, reference numeral 4 denotes the subject, 5 denotes an affected part, and 7 denotes a slice position for the CT apparatus 21. Reference numeral 70 denotes tomography images made by the CT apparatus, and 50 denotes a tomography image of the affected part. Reference numeral 8 denotes an area of interest set within the outline of the tomography image 50 of the affected part on the tomography image 70, and 9 denotes a marker set on the subject. Also, reference numeral 71 denotes 3-D data relating the subject 4 obtained by interpolating tomography images 70, 81 denotes a 3-D area of interest obtained by interpolating the area of interest 8, and 85 denotes the center of the area of interest. "S" represents a hypothetical center-of-projection point removed from the center 85 of the area of interest in a desired direction by a desired limited distance SAD (i.e., having desired geometric conditions), 10 denotes a hypothetical projection plane set perpendicular to a straight line connecting the center-of-projection point S and center 85 of the area of interest, 11 denotes a projected image of the 3-D data 71 relating to the subject 4 projected on the projecting plane 10 by calculation, and 12 denotes a projected image of the of the area of interest 81 projected by calculation. Also, 60 denotes laser beams cast from three directions (i.e., from the left, right, and above) onto the center 85 of the area of interest, and 6 denotes an iso-center mark applied to the surface of the subject following the laser beams.

The action flow of the therapy plan will be described with reference to FIG. 2. Of the overall therapy plan, this shows the center projection image creating unit and the projection unit of the output unit. First, the area of interest (target) is set-and input (S1). Next, the center of the area of interest is calculated as an iso-center (S2), and the rotational angle of the gantry and the like is input with the hypothetical radiation beam source as the center-of-projection point, whereby the position of the hypothetical radiation beam source at that position (center-of-projection point) is calculated (S3). The offset calculation from a reference position to the center of the area of interest is performed by making offset calculation from the reference position to the iso-center, i.e., parallel movement (S4). Calculation of rotation according to the direction of the center-of-projection point is made by calculation of rotation according to the direction of the center-of-projection point (hypothetical beam source), i.e., rotational movement (S5). Next, a beam element connecting the center-of-projection point and the projection plane is selected (S6), and correction and addition of the CT value of the voxel intersecting with the beam element is performed (S7). This is performed for all voxels on the beam element (S8). Then, calculation is made for all valid pixels on the projection screen, and the flow ends (S9).

The position of the marker is identified from the calculated screen (S10), this projection image is output to a recording medium (S11), and the obtained image is projected as an output image of an optical system having the same geometric conditions as the center-of-projection point (S12).

As shown in FIG. 3A, The subject 4 and the affected part 5 therein and the marker 9 are scanned by the CT apparatus 21 at multiple slice positions 7 so as to create 3-D data 71. The subjected is fastened to a fastening jig not shown in the Figures. While watching the tomography images 70 shown in FIG. 3B on the display unit 25 of the therapy planning apparatus, the operator estimates and inputs the affected part 50 as the area of interest 8, using the keyboard and mouse 26. New data is created for distinguishing the area of interest 8 from other areas. When input of the area of interest 8 is completed, the calculation processing unit 24 acts to obtain the center 85 of the area of interest, as shown in FIG. 3C. When the center 85 of the area of interest has been obtained, laser beams 60 are cast from laser beam generating devices not shown in the Figure which have received data regarding the affected portion at the center of the Figure, onto the portion of the subject 4 secured to the fastening jig corresponding with the center 85 of the area of interest. An iso-center mark 6 is applied to the portion on the surface of the subject 4 to which the laser beams 60 are cast. Next, the position of the point of origin for generating radiation beams to be irradiated onto the affected part 5 of the subject 4 is determined, and the limited distance SAD corresponding with the center 85 of the area of interest and the direction thereof are input by the keyboard and/or the mouse 26. That is, the geometric conditions for the area of interest 81 of the center-of-projection point S are equal to the geometric conditions for the point of origin for generating radiation beams to be irradiated onto the affected part 5 of the subject 4. The projection images 11 and 12 are projected on the projection plane 10, and are determined by the following elements: the coordinates of the center-of-projection point S, the coordinates of the center 85 of the area of interest, 3-D data, and area of interest 81. The projection images 11 and 12 are calculated by the calculation processing unit 24, based on the above elements. Particularly, the projection image 12 is a projection of the area of interest 81, and is displayed in a manner distinguished from the other projection image 11, by projecting with reference to data distinguishing the area of interest 81 from other areas. Accordingly, the projection image 12 can be clearly distinguished from the projection image 11 of other 3-D data. Accordingly, even in cases wherein there is no difference in contrast between the affected part 5 and other parts, the surroundings of the affected part 5 can be identified from the projection images 11 and 12. The projection images 11 and 12 are enlarged or reduced at a desired ratio input from the keyboard 26, and output to the recording medium 27 by the output device provided to the therapy planning apparatus.

Figure 4:
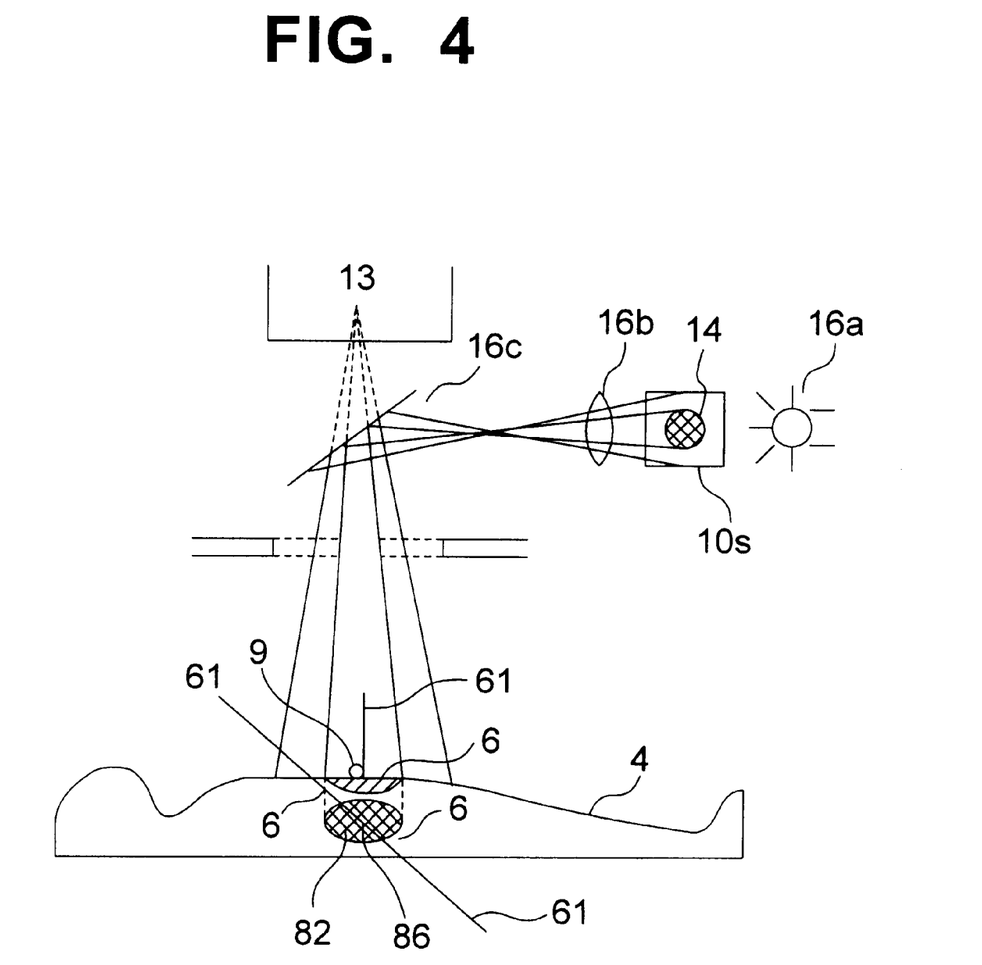
FIG. 4 is a diagram describing an embodiment of the radiation therapy apparatus according to the present invention.

FIG. 4 illustrates an embodiment of the projection image displaying method and radiation therapy apparatus using the above-described projection image synthesizing method, showing the parts not shown in FIG. 3. Reference numerals which are the same as those in the above description denote the same members. In FIG. 4, reference numeral 82 denotes a corresponding area of the subject 4 that corresponds with the area of interest 81, 86 denotes the center of the corresponding area 82 of the subject 4 that corresponds with the center 85 of the area of interest, and 13 denotes the X-ray generating source of the radiation beam area device, and the position, i.e., geometric conditions regarding the corresponding area 82 and center 86 of corresponding area is equal to the geometric conditions regarding the area of interest 81 of the center S of projection and the center 85 of the area of interest. Also, 10s denotes film upon which projection images 11 and 12 obtained by the above projection image displaying method and radiation therapy apparatus and reduced by a desired ratio have been projected, and 16a through 16c denote an optical system for projecting the images photographed on the film with the X-ray generating source 13 as the center of projection, wherein 16a denotes a lamp, 16b a lens, and 16c a mirror. Reference numeral 14 represents a projection image of the area of interest 85 projected by the film 10s and the optical system 16a–16c. The fastening jig of the radiation therapy apparatus is used to secure the subject 4 so as to match the iso-center mark 6 with the laser beams 61. The film 10s is set in the film holding unit of the radiation therapy apparatus. The projection images 11 and 12 photographed on the film 10s are projected on the subject 4 by the optical system 16a–16c. At the time of conducting irradiation of radiation, the collimator aperture for the radiation beam is adjusted according to the projected images. Projection of the projection images 11 and 12 on the surface of the subject 4, irradiation of X-rays to the corresponding area 82, and calculated projection according to the center-of-projection point S of the area of interest 81, are the same as these geometric conditions. Thus, according to the projection image displaying method and radiation therapy apparatus, determination of the radiation display area becomes even easier.

Also, in the event of changing the angle of the gantry and performing multiple-field irradiation, images are prepared for each angle, and projection is performed when the set angle is reached.

Leaving the marker 9 on the surface of the subject 4 from the time of making the therapy plan to the time of performing therapy allows irradiation to be controlled by comparing the position of the projected marker and the position of the actual marker 9. In other words, irradiation is conducted when the marker positions match, and is terminated when the marker positions shift, so irradiation can be carried out while compensating for movement in the affected part owing to bodily movement, thereby avoiding erroneous irradiation to normal cells.

Figure 5A:
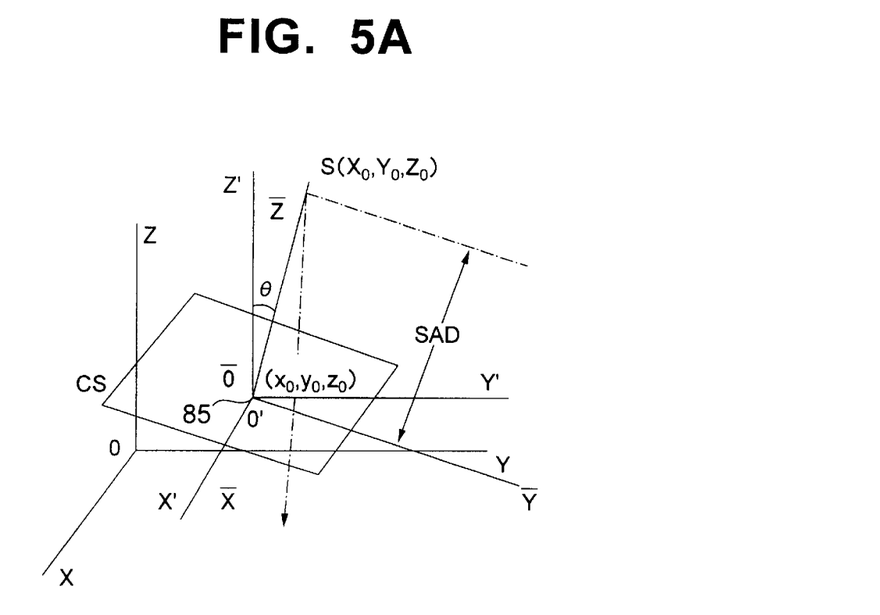
FIGS. 5A and 5B are diagrams illustrating conversion of coordinates for creating a projection image with a CT apparatus.
Figure 5B:
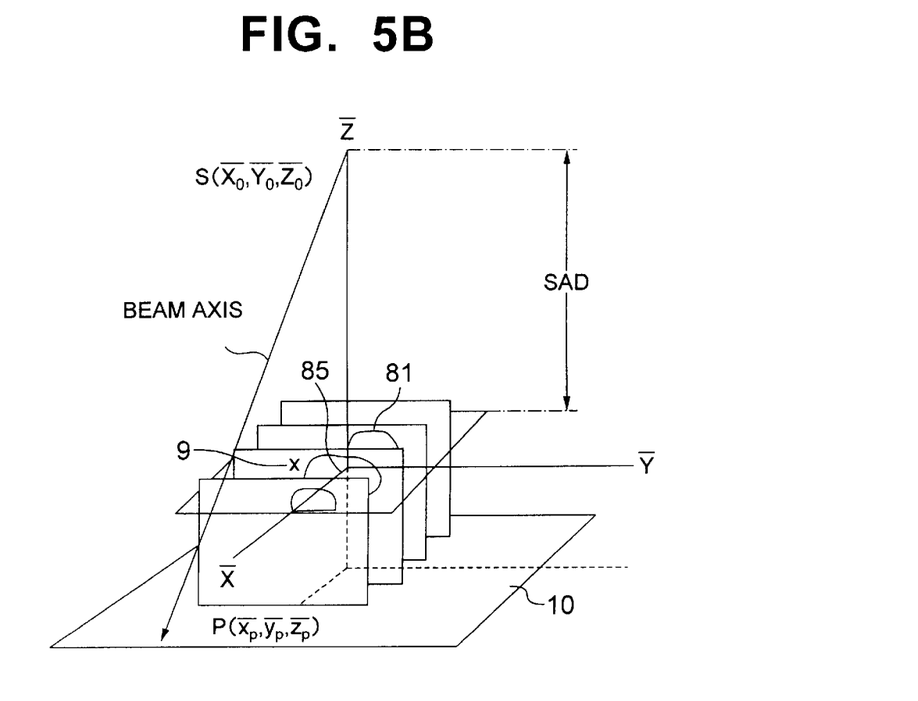

Next, description will be made regarding projection image synthesizing with the projection image synthesizing method and apparatus. FIG. 5A shows coordinates conversion from CT coordinates O-XYZ from a CT apparatus to CS (Computed Simulation) coordinates O-XYZ for creating a projected image. Conversion of the coordinates axis consists of the following two: parallel movement of the point of origin to the center 85 of the area of interest (i.e., movement from O-XYZ to O'-X'Y'Z'); and rotation owing to the direction of irradiation of radiation, i.e., the relative position of the center-of-projection point S (i.e., movement from O'-X'Y'Z' to O-XYZ). FIG. 5B shows the way in which the image is projected. In the direct coordinates O-XYZ, the center-of-projection point is represented by $S(X_o, Y_o, Z_o)$, and the projected image projected from that point S is represented by coordinates $P(X_P, Y_P, Z_P)$. Next, a straight line passing through points P and S is called a beam element, and the coordinates of the points on the beam element are obtained. Obtaining the coordinates of the points on the beam element facilitates obtaining of the coordinates of all of the voxels in the 3-D data and area of interest 81 through which the beam element passes.

Figure 6A:
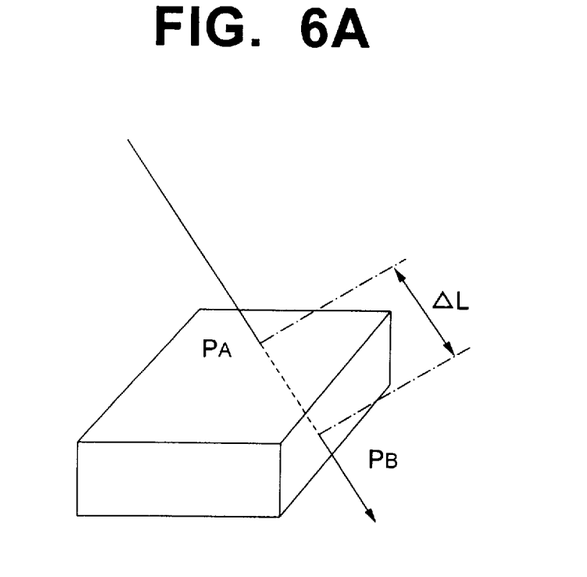
FIGS. 6A and 6B are diagrams illustrating correction of CT values in accumulation of CT values on beam elements.
Figure 6B:
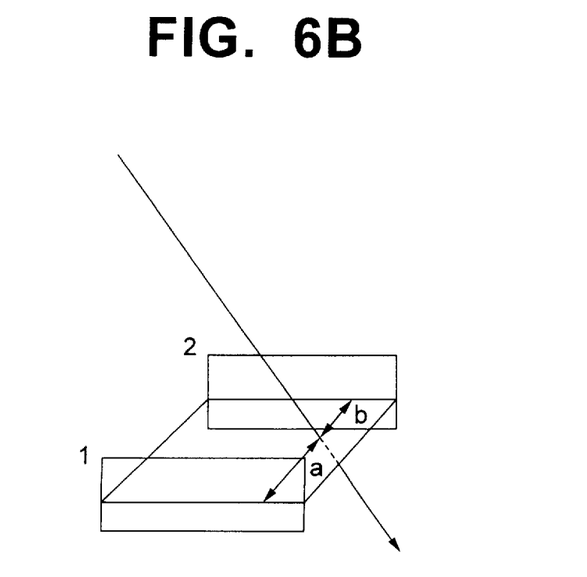

The projection images 11 and 12 are obtained by accumulating the CT values of the voxels on the beam element. FIGS. 6A–6B illustrate correction of the CT values in accumulation of the CT value on the beam element. With regard to FIG. 6A, the rectangular entity is a voxel (a unit of 3-D data) obtained by interpolating between the tomography images from the CT apparatus in 1 mm slices. The CT value of the interpolated voxel comprises proportional distribution according to the distance from the tomography image. $P_A$ denotes the entrance to the voxel, and $P_B$ denotes the exit from the voxel. AT this time, the length $\Delta L$ of the beam element crossing the voxel is divided by the volume V of the voxel, and the value thus obtained is multiplied by the CT value n. This value, i.e., $(n/V)\Delta L$, is integrated in the range that tomography images exist, thereby obtaining an image pixel value $\Sigma(n/V)\Delta L$ of a pixel of the projection image. The CT values in the area of interest 81 have been re-colored to extreme values (i.e., either white or black), so the area of interest can easily be distinguished from the other parts, even on the -projected image. Also, such processing can be performed with multiple voxels in mind. In such a case, the value n is made to be an average CT value from multiple voxels. 6B illustrates other correction of the CT values in accumulation of the CT value on the beam element. In the Figure, "a" denotes the distance from pixel 1 to the beam element intersection, and "b" denotes the distance from pixel 2 to the beam element intersection. A plane is created between the pixels of each tomography image, and the CT value is distributed by the ratio of the distance from the tomography image of the point at which the beam element crosses the plane. The former correction has excellent resolution, and thus is suitable for use on the head. The later correction has little noise, and thus is suitable for use on the abdomen.

The projection image is completed when the above processing is performed for the pixels within a certain range on the projection plane 10 and the pixel values are obtained.

It should be noted that the present invention is by no means restricted to the above embodiment. The 3-D data relating to the inside of the body of the subject 4 may be multiple tomography images from X-ray CT, or may be from MRI (Magnetic Resonance Imaging). Also, the projection image synthesizing apparatus and projection image display apparatus may be free-standing apparatuses, or a CT apparatus and accessory equipment; and the equipment may be integrated into a single apparatus or may be a collection of multiple apparatuses. Also, the voxels in the area of interest may be replaced with drastically great (or small) gradient data and thus be projected. Also, the voxels in the area of interest may be loaded with identification signals other than the gradient data, so as to judge whether or not a voxel with identification signals exists on the beam element. With such an arrangement, even in the event that there is only one area-of-interest voxel on the beam element, a different display can be made on the projection image. Also, the image may be inverted when photographing with the film. Also, output of the projection image may be in the form of on-line image signals, rather than photography using film. The projection thereof may be an arrangement wherein an image displayed on a CRT is projected with an optical system such as a projector or the like, or image signals may be input to a transmitting liquid crystal panel and projected. Also, signals relating to the projection image 12 of the area of interest 81 may be input, thus facilitating ease in controlling the aperture form of the collimator of the radiation beam irradiation apparatus.

Second Embodiment

Figure 7:
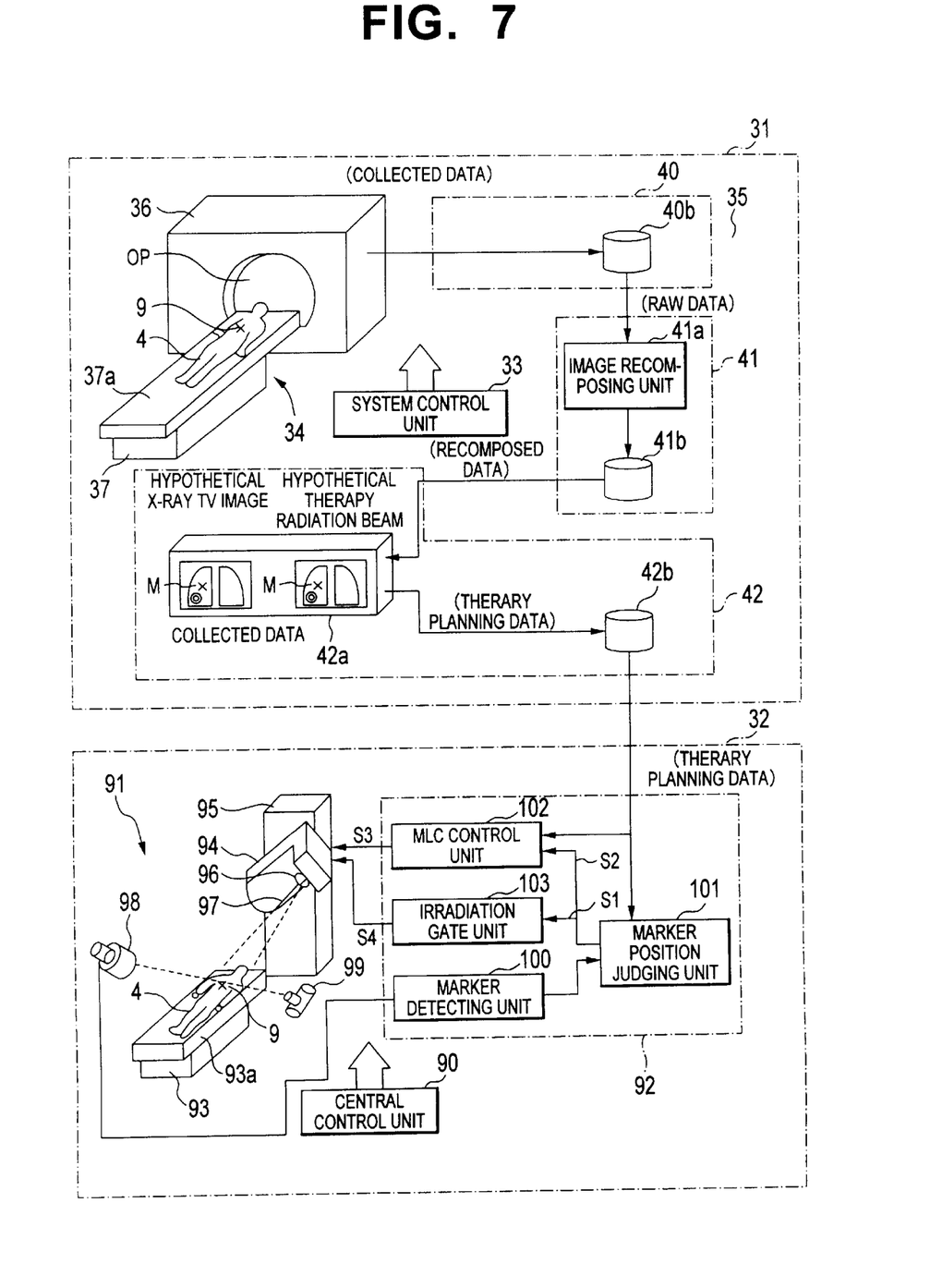
FIG. 7 is a diagram illustrating the configuration of a radiation therapy system according to the present invention.

The radiation therapy system shown in FIG. 7 has a radiation therapy planning CT system 31 for carrying out consistent radiation therapy from the point of obtaining images to positioning (simulation), and a radiation therapy apparatus 32 which conducts radiation therapy according to the therapy planning data planned and simulated with the radiation therapy planning system 31. The radiation therapy planning system 31 and the radiation therapy apparatus 32 are connected one to another via coaxial cabling and a network or the like so as to be capable of communication. However, these need not necessarily be arranged so as to be capable of communication; rather, examples of non-on-line arrangements include passing information through a portable medium such as magnetic disks, MO disks, optical disks, and so forth, that are capable of recording therapy planning data, for example. The radiation therapy planning CT system 31 (hereafter referred to simply as "CT system") is comprised of a system control unit 33 centrally controlling the overall CT system 31, a CT scanner unit for obtaining image data for the therapy plan, and a therapy planning unit 35 for processing the data obtained by the CR scanner unit and creating therapy planning data.

The system control unit 33 is comprised of a single computer, for example, whereby processing is conducted following programs stored in the memory thereof beforehand. The various control signals thus obtained are output to the CT scanner unit 34 and the therapy planning unit 35.

The CT scanner unit 34 has at least a gantry 36 and bed 37, and is driven by the R—R method for example, based on control signals from the control unit 33 given via multiple control units (e.g., X-ray, bed, frame, etc.) not shown in the Figure.

The gantry 36 has built in an unshown X-ray tube and X-ray detector, positioned facing one another across the subject 4 inserted from the diagnosing opening OP. Minute current signals which are equivalent to the transmitted X-rays detected with the X-ray detector are converted to digital quantities in an unshown data collecting unit within the gantry 36, and are sent to the therapy planning portion 35 as collected data to be used for the CT image.

The therapy planning portion 35 creates therapy planning data based on the collected data for the CT image that is sent from the CT scanner unit 34, and is comprised of a raw data unit 40, image recomposing portion 41, and therapy planning unit 42.

The raw data unit 40 has a disk unit 40b. This disk unit 40b has a large-capacity disk such as an optical disk, and is arranged so as to store the collected data as raw data, and supply the raw data to the image recomposing portion 41.

The image recomposing portion 41 has an image recomposing unit 41a and a disk unit 41b. The image recomposing unit 41a is comprised of a single computer, for example, whereby, following programs stored in the memory thereof beforehand, the raw data from the raw data unit 40 is reconstructed as CT images including multiple slice planes (n slice planes) G1 through Gn.

The disk unit 41b has a large-capacity disk such as an optical disk, and is arranged so as to store the recomposed data from the image recomposing unit 41a, and supply the recomposed data to the therapy planning unit 42.

The therapy planning unit 42 has a planning portion 42a and disk portion 42b. The planning portion 42a is comprised of a single computer, for example, whereby processing is performed following radiation therapy planning programs stored in the memory thereof beforehand.

In other words, this planning portion 42a displays the recomposed image data, i.e., the slice planes G1 through Gn from the image recomposing portion 41, and at the same time creates planning data K1 through Kn including collimator open/close data L1 through Ln corresponding with each of the images of the slice planes G1 through Gn.

The slice planes G1 through Gn on which the planning data K1 through Kn thus created are added to the created planning data K1 through Kn, and are sent to the disk portion 42b as therapy planning data D1 through Dn. This disk portion 42b has a large-capacity disk such as an optical disk, and is arranged so as to store the therapy planning data D1 through Dn from the planning portion 42a, and supply the recomposed data to the radiation therapy apparatus 32.

The radiation therapy planning apparatus 32 (hereafter referred to simply as "therapy apparatus") uses X-rays for therapy in the present embodiment, and is comprised of a central control unit 90 for controlling the overall therapy apparatus 32, an apparatus proper 91 for actually carrying out the therapy based on the therapy planning data D1 through Dn created by the CT system 31, and a driving control unit 92 for controlling the various types of driving of the apparatus proper 91.

The central control unit 90 is comprised of a single computer, for example, whereby processing is performed following programs stored in the memory thereof beforehand. This central control unit 90 is capable of received the therapy planning data D1 through Dn created by the CT system 31, and supplies control signals based on this therapy planning data to the apparatus proper 91 and driving control unit 92.

The apparatus proper 91 has a therapy table 93 on which the subject 4 is mounted, a rotatable frame 94 which rotates with the body axis direction of the subject 4 as the rotational axis thereof, and a frame support 95 for rotatably supporting the frame 94.

The therapy table 93 has a lid 93a toward the top thereof. The height of the therapy table 93 can be adjusted by an internal driving mechanism, so the lid 93a can thus be vertically moved. Also, the therapy table 93 can move the lid 93a in the longitudinal and sideways directions within certain ranges by means of a separate internal driving mechanism, and can rotate around the lid-supporting posts and iso-center, by operating yet another driving mechanism. These operations of the lid 93a are necessary for positioning the subject 4 on the lid and for irradiating radiation, and control is made by control signals supplied from the central control unit 90 via the driving control unit 92.

On the other hand, the frame 94 has an irradiation head 96 for deflecting accelerated electrons from an accelerating tube so as to strike a target, and irradiating the X-ray beams thus generated on the subject 4. This irradiation of X-ray beams is performed based on control signals S4 from an irradiation gate 103 described later. Also, a collimator 97 for determining the field of irradiation on the surface of the subject 4 is provided between the target, i.e., the radiation source and the irradiation opening on the irradiation head 96. This collimator 97 in the present embodiment is a multi-leaf collimator having the structure of a hyper-fractionated principal aperture.

This multi-leaf collimator is comprised such that two types of leaf groups each formed of tungsten alloy or iron leaves forming multiple plates are positioned juxtaposed across the X-ray path from the radiation source, with each of the leaves being independently driven in the longitudinal direction of each leaf by means of a moving mechanism having a leadscrew as the principal portion thereof, for example. This moving mechanism is driven according to control signals S3 supplied from the later-described collimator control unit 102, so as to change the size and form of the irradiation opening formed by the two leaf groups (i.e., equivalent to the size and form of the irradiation field) in real-time. The driving portion may be arranged such that the leaves are provided with saw-tooth notches to be driven by gears, instead of the leadscrew.

Further, the frame support 95 is arranged so as to be capable of rotating the entire frame 94 in either clockwise or counter-clockwise directions, by means of an internal driving mechanism. Operation of this driving mechanism is carried out based on control signals supplied from the central control unit 90 via the driving control unit 92.

The driving control unit 92 has multiple unshown control units for performing tasks appointed to each based on the instructions of the central control unit 90, e.g., control units for the klystron, therapy table, frame, etc. Each of these multiple control units are comprised of a single computer, for example, whereby processing is performed following programs stored in the memory thereof beforehand. Of the multiple control units, the control units according to the present embodiment includes a marker detecting unit 100, marker position judging unit 101, multi-leaf collimator control unit 102 (hereafter simply referred to as "collimator control unit"), and irradiation gate unit 103.

The marker detecting unit 100 detects the marker 9 established on the subject 4 by fluoroscopy with an X-ray TV 98, X-ray tube 99, etc., and outputs this to the marker position judging unit 101.

The marker position judging unit 101 constantly compares the marker position data M1 through Mn within the therapy planning data D1 through Dn supplied from the CT system 31 beforehand with the marker position data Kd sent from the marker detecting unit in real-time, and constantly judges the correlation between both sets of data. Then, at the point that judgment is made that there is correlation with, e.g., the marker position data Ma, of the marker position data M1 through Mn, a control signal S1 is turned on, and a control signal S2 for specifying the collimator open/close data La within the therapy planning data Da corresponding to the marker position data Ma is output to the collimator control unit 102, in the next step.

The collimator control unit 102 has collimator open/close data L1 through Ln within the therapy planning data D1 through Dn supplied from the CT system 31 beforehand, and holds this in memory, for example, so as to specify the collimator open/close data La corresponding to the control signal S2 from the above maker position judging unit 101, and output a control signal S3 to the apparatus proper 91 for opening/closing the collimator 97 according to this open/close data La.

While the therapy apparatus 32 is running, the irradiation gate unit 103 outputs a control signal S4 to the apparatus proper 91, and also is energized by the marker position judging unit 101 turning the control signal S1 on so as to turn the control signal S4 on. The apparatus proper 91 is energized by this control signal S4 being turned on, and this irradiates an X-ray beam from the irradiation head onto the subject 4. While the above example involves moving the collimator, movement of the affected part owing to bodily movement may be chased by moving the therapy table.

Next, the overall operation of the present embodiment will be described with reference to FIG. 8.

First, description will be made from the time of obtaining data to the time of therapy planning.

First, the CT system is energized by the various control signals from the system control unit 33, and collected data regarding the subject 4 is generated. This collected data is supplied to the therapy planning unit 35, and recomposed as a plurality of slice planes.

Figure 8:
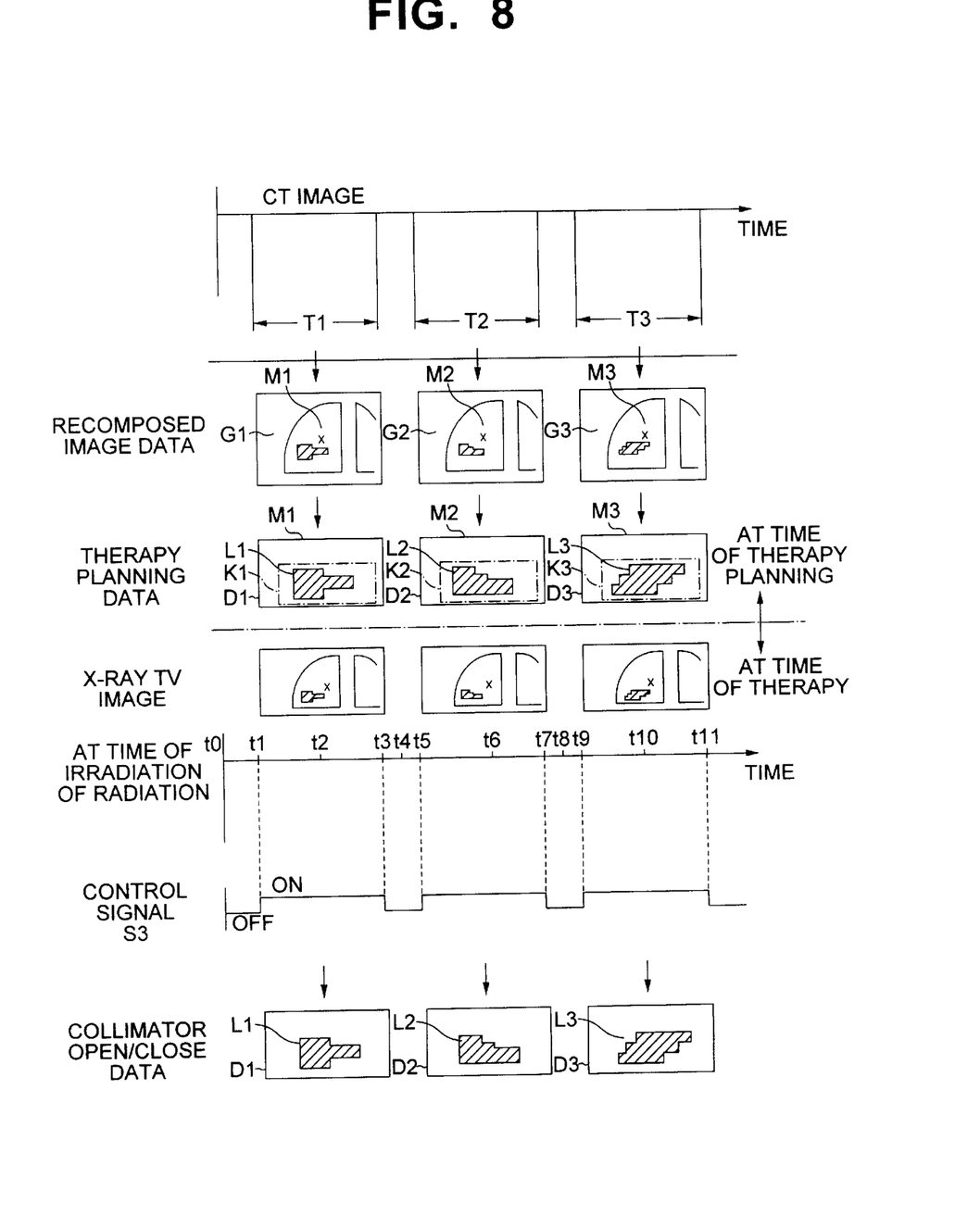
FIG. 8 is a diagram illustrating the operation of the radiation therapy system according to the present invention.

Let us say that, of the recomposed plurality of slice planes, three slice planes, G1, G2, and G3 are selected for the therapy planning shown in FIG. 8. These three slice planes G1, G2, and G3 are correlated with on the collection data obtaining periods T1, T2, and T3, upon which each is based.

Based on the above three slice planes G1, G2, and G3, planning data K1, K2, and K3, including collimator open/close data L1, L2, and L3 is generated for each of the planes. This planning data K1, K2, and K3 is supplied to the therapy apparatus 32 along with marker positions M1, M2, and M3, as therapy planning data D1, D2, and D3.

Next, description will be made regarding the time of irradiation of radiation.

Now, let us say that the therapy apparatus 32 is activated at a certain time t0. At the time of activation thereof, the marker 9 established on the subject 4 is subjected to fluoroscopy-with an X-ray TV 98, X-ray tube 99, etc., and marker position information Kd is detected in real-time by the marker position detecting unit 101. The detected marker position information Kd is compared with each of the position data M1, M2, and M3 from the CT system 1 in the marker position detecting unit 101, and as long as judgment is made that there is no correlation with any of these, the control signal S1 remains connected in the off state, so there is no generating of the control signal S2, either. Accordingly, the control signal S4 from the irradiation gate unit 103 remains off, and there is no irradiation of X-rays from the apparatus proper 91 to the subject 4.

Next, at a time t1, judgment is made by the marker position judging unit 101 that there is correlation between the position data Kd and the marker position M1 at the marker detecting unit 100, and the control signal S1 is turned on. Synchronously with this turning on, a control signal S2 instructing the collimator open/close data L1 within the therapy planning data D1 corresponding to the position of the position data M1 is output to the collimator control unit 102.

A control signal S3 is generated at the collimator control unit 102 in accordance with the control signals S1 and S2, and opening/closing of the collimator 97 is instructed based on the open/close data L1, and at the same time, a control signal S4 from the irradiation gate unit 103 to the apparatus proper 91 is turned on, thereby conducting irradiation of X-ray beams. This irradiation of X-ray beams is continued past a certain time t2 until a time t3.

Next, at the time t3, the control signal S1 turns off, and synchronously with this turning off, the output of the control signal S2 to the collimator control unit 102 stops. Accordingly, control signals S3 are not generated, and the control signal S4 turns off, so irradiation of X-ray beams stops. This stopped state is continued past a certain time t4 until a time t5.

Next, at the time t5, judgment is made by the marker position judging unit 101 that there is correlation between the position data Kd and the marker position M2 at the marker detecting unit 100, and the control signal S1 is turned on. Synchronously with this turning on, a control signal S2 instructing the collimator open/close data L2 within the therapy planning data D2 corresponding to the position of the position data M2 is output to the collimator control unit 102.

A control signal S3 is generated at the collimator control unit 102 in accordance with the control signals S1 and S2, and opening/closing of the collimator 97 is instructed based on the open/close data L2, and at the same time, a control signal S4 from the irradiation gate unit 103 to the apparatus proper 91 is turned on, thereby conducting irradiation of X-ray beams onto the subject 4. This irradiation of X-ray beams is continued past a certain time t6 until a time t7.

Next, at the time t7, the control signal S1 turns off, and synchronously with this turning off, the output of the control signal S2 to the collimator control unit 102 stops. Accordingly, control signals S3 are not generated, and the control signal S4 turns off, so irradiation of X-ray beams stops. This stopped state is continued past a certain time t8 until a time t9.

Next, at the time t9, judgment is made by the marker position judging unit 101 that there is correlation between the position data Kd and the marker position M3 at the marker detecting unit 100, and the control signal S1 is turned on. Synchronously with this turning on, a control signal S2 instructing the collimator open/close data L3 within the therapy planning data D3 corresponding to the position of the position data M3 is output to the collimator control unit 102.

A control signal S3 is generated at the collimator control unit 102 in accordance with the control signals S1 and S2, and opening/closing of the collimator 97 is instructed based on the open/close data L2, and at the same time, a control signal S4 from the irradiation gate unit 103 to the apparatus proper 91 is turned on, thereby conducting irradiation of X-ray beams onto the subject 4. This irradiation of X-ray beams is continued past a certain time t10 until a time t11.

Next, at the time t11, the control signal S1 turns off, and synchronously with this turning off, the output of the control signal S2 to the collimator control unit 102 stops. Accordingly, control signals S3 are not generated, and the control signal S4 turns off, so irradiation of X-ray beams stops.

The above operation is consecutively repeated during the irradiation of radiation. Accordingly, even in the event that the affected part such as a cancer tumor moves or is deformed, the irradiation state based on the therapy planning data made beforehand according to the position of the marker 9 at the time of bodily movement of that part can be instructed in real-time according to the marker position at the time of bodily movement, so sufficient and precise irradiation of radiation can be performed to the part which is the target, regardless of bodily movement of the patient. Also, unnecessary irradiation of radiation can be suppressed, so the amount of bombardment to the patient can be minimized. Also, in the event that the area of interest shifts from the target due to bodily movement, the method of stopping irradiation of radiation can be controlled by an unshown triode electron gun grid. In the case of a diode electron gun, the high-voltage pulses applied may be controlled. The irradiation of radiation resumes when the area of interest returns to the original position.

Incidentally, though the present embodiment involves outputting control signals S2 to the collimator control unit 102 according to control signals S1 from the marker position judging unit 101, the present invention is by no means restricted to this arrangement.

That is, the arrangement may be such that opening/closing of the collimator 97 is performed taking into consideration the amount of time required from the time of receiving the control signal S3 from the collimator control unit 102 till the actual opening/closing of the collimator 97 according to the open/close data.

An arrangement also may be employed wherein the value set for the collimator is fixed, and irradiation is performed only when the marker position viewed by fluoroscopy with the X-ray TV matches the marker position Kd corresponding with this opening.

In the above embodiment, the marker 9 has been described as being singular, but two or more may be used.

Also, the present embodiment has been described as obtaining a fluoroscopy image by an X-ray TV 98 and X-ray tube 99, but other fluoroscopy image obtaining methods such as echo or ultrasonic methods may be used, with equal advantages.

Also, the form of the marker 9 is preferably a needle-shaped member or a ball of around 2 mm in diameter being inserted into the body, but other arrangements may be used, instead.

Also, the present embodiment has been described with regard to a case wherein X-rays are irradiated, but proton beams or heavy corpuscular rays may be used, with the same advantages.

Also, the x-ray TV described in the present embodiment is a single-type, but a double-type may be used, to determine the position of the marker in 3-D. Also, employing a triple-type or higher allows 3-D positioning using something else for the X-ray TV which is not visible when the gantry rotates.

The present invention configured as described above has the following advantages.

A projected image with the same conditions as irradiation of radiation beams is synthesized from 3-D data of the subject and the marker, and/or the area of interest therein, so the fluoroscopy image has the same perspective as a radiation fluoroscopy image or X-ray TV radiation fluoroscopy image, and thus a projection image for the position and range of the area of interest can be obtained in a clear manner. Accordingly, this arrangement is suitable for determining the range of the position of irradiation of radiation, in the case of aiming at a certain portion within the body of the subject and performing irradiation of radiation.

Also, the image can be photographed on film at an enlargement/reduction of a desired ratio, so film can be used regardless of the size of the optical system.

Further, according to the projection image synthesizing method and apparatus, the projection image is projected onto the surface of the subject under the same conditions as the irradiation of radiation, so even though the surface of the subject is not flat, the radiation irradiation position and range can be displayed easily, quantitatively, and precisely, in comparison with the marker established on the surface of the body.

According to the present invention, CT images of the subject which change over time are obtained, and a center projection image with the same conditions as the irradiation of radiation at the same time, and a center projection image with the same conditions as the X-ray TV are synthesized, and therapy planning data including opening/closing data of the collimator is created based on the projection image with the same conditions as the irradiation of radiation, so as to control the irradiation state of radiation in real-time according to this created therapy planning data and the movement of the marker viewed by fluoroscopy with the C-ray TV during irradiation, whereby irradiation of radiation can be conducted to the part of the patient that is the target regardless of the bodily movement of the patient in a sufficient and precise manner. This suppresses unnecessary irradiation of radiation, so the amount of bombardment of the patient can be minimized, thereby markedly improving the precision of radiation treatment.

What is claimed is:

1. A radiation therapy system using a center projection image synthesizing method for creating an image for determining the range of irradiation of radiation beams, in an arrangement wherein irradiation of radiation beams is aimed at a specific portion within the body of a subject, said system comprising:

a means for establishing a marker at said specific portion including the surface of said subject, and for specifying as an area of interest an area corresponding with said specific portion in 3-D data regarding inside of the body of said subject which has been obtained with a CT apparatus; and a means for calculating a projection image for said area of interest according to a center-of-projection point at geometric conditions set for the area of interest and said marker, and/or said 3-D data;

wherein said geometric conditions are the same as the geometric conditions for the point of origin for irradiation of radiation beams to the portion corresponding with the area of interest in the body of the subject.

2. The radiation therapy system according to the claim 1, further comprising means for enlarging or reducing the size of said projection image by a desired ratio and outputting to a recording medium.

3. A radiation therapy system using a center projection image synthesizing method for creating an image for determining the range of irradiation of radiation beams by aiming X-rays at a specific portion within the body of a subject, said system comprising:

a means for establishing a marker at said specific portion including the surface of said subject, and for specifying as an area of interest an area corresponding with said specific portion in 3-D data regarding inside of the body of said subject which has been obtained with a CT apparatus; and a means for calculating a projection image for said area of interest according to a center-of-projection point at geometric conditions set for said area of interest and said marker, and/or said 3-D data;

wherein said geometric conditions are the same as the geometric conditions for the focal point of an X-ray tube in an X-ray TV apparatus on the portion corresponding with the area of interest in the body of the subject.

4. The radiation therapy system according to the claim 3, further comprising means for enlarging or reducing the size of said projection image by a desired ratio and outputting to a recording medium.

5. A radiation therapy system, comprising:

a means for establishing a marker at a specific portion in the body of a subject including the surface of said subject, and for specifying as an area of interest a desired area in 3-D data regarding inside of the body of said subject which has been obtained with a CT apparatus; and a means for projecting a projection image on the surface of said subject by means of an optical system which has conditions that are the same as said geometric conditions for the specific portion corresponding with the area of interest in the body of subject according to the center-of-projection point of the geometric conditions set for the area of interest, wherein the center-of-projection point thereof matches the point of origin for generating radiation beams.

6. The radiation therapy system according to the claim 5, further comprising means for enlarging or reducing the size of said projection image by a desired ratio and outputting to a recording medium.

* * * * *